United States Patent [19]

Hetherington

[11] Plant 5,154

[45] Dec. 6, 1983

[54] PAMELA HETHERINGTON CORONATION

[75] Inventor: Ernest E. Hetherington, Arcadia, Calif.

[73] Assignee: Fred A. Stewart Inc., San Gabriel, Calif.

[21] Appl. No.: 396,241

[22] Filed: Jul. 8, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Edmond F. Shanahan

[57] ABSTRACT

A new and distinct variety of orchid, and more particularly a Brasso-laeliocattleya (Blc.) hybrid plant which is outstanding and distinct from other orchids because of its superior flowers, which combine a rare coloring, massive size, and profusion of flowers on a single stem. The coloring is mostly a delicate lilac-rose surrounding a central white and yellow area, as specifically described hereinafter. The new variety is also distinctive from its parent population and similar hybrids by its outstanding plant structure. Its flowers are of exceptional substance (thicker and more resilient petals than related plants); they are perfectly placed on the stem; the stem is superior to its relatives in strength; the flowers have a longer bloom life, and are produced more abundantly than orchids of the nearest similar breeding.

2 Drawing Figures

DISCOVERY OF THE NEW VARIETY

The orchid of this application was discovered by the undersigned discoverer in 1970 as an outstanding member of a large sibling population of the hybrid Brassolaeliocattleya Pamela Hetherington (hereinafter abbreviated Blc. Pamela Hetherington), all cultivated and blooming at the Stewart Nursery in San Gabriel, Calif.

Crossing of Blc. Pamela Hetherington, from which the sibling variety 'Coronation' was selected, was originally sown at the orchid nursery of Fred A. Stewart Inc. at San Gabriel, Calif., in 1966, by crossing Laeliocattleya Paradisio 'Colossal' as the pod parent by Brassocattleya Mount Anderson as the pollen parent. It was registered by the Stewart Nursery with the Registration Committee for Orchids of The Royal Horticultural Society, London, England, on Oct. 27, 1970, as "Stewart cross #1253", Blc. Pamela Hetherington.

The plant of the new variety was immediately recognizable as superior in its flowers to all other members of that population group of the hybrid Blc. Pamela Hetherington. After the new variety had been observed, its other features of superior growth and structure were noted. The varietal name 'Coronation' was added to the hybrid's name to identify the new variety of this application.

ASEXUAL REPRODUCTION

After the 'Coronation' variety was discovered and named in late 1970, the original plant was placed in the laboratories of Fred A. Stewart Inc. Nursery. During the following years, a large number of plants have been asexually produced by the meristem tissue culture method. Portions of tissue, called meristem, and comprised of unspecialized cells capable of later differentiation, were cut from the original plant, and developed under carefully controlled sterile conditions, into new individual plants, which served, in turn, as additional sources of meristem culture.

All the propagations thus produced have reproduced true to the original plant in both plant and flower. A substantial cross-section has been flowered; they are exactly the same as the mother clone. All plants of the new variety have continued to be readily distinguishable from both parents, and from siblings of Blc. Pamela Hetherington populations.

DESCRIPTION OF THE PHOTOGRAPHS

The upper photograph is a close-up view of two large flowers typical of the new variety.

The lower photograph shows the same flowers, but as viewed from a greater distance, so as to reveal the appearance of the plant as a whole.

Both photographs show the plant adjacent a Christmas tree, since one outstanding feature of the variety is that its main blooming season is December.

DESCRIPTION OF THE PLANT

In some respects, the plant of the new variety, Coronation, is typical of Cattleya orchids. Its leaves are strapped, unifoliate, and coriacious. The leaves, at full growth, are typically 30 to 35 centimeters long. The plant attains a height of 45 to 60 centimeters at maturity. However, the stems, flower sheaths, leaves, and other parts of the plant structure are heavier and thicker in appearance than other Pamela Hetherington orchids. The Coronation variety exhibits greater strength and resilience, than all other varieties of Pamela Hetherington orchids. The rhizone is sturdy, branching off into flowering leads. The growth habit is compact and naturally erect. The plant has a stem which bears the massive flowers without any support. The growths are of such substance along with the sheath from which the flower spray develops that the flowers are carried erectly and well spaced above the foliage and separate from other flowers in bloom on the plant at the same time.

The plants have been hardy in comparison with other similar orchids. Blc. Pamela Hetherington plants, both in the original population and in the new variety, have been virus and pathogen free during development. The cells have an even chromosome compliment, which is associated with the uniform, strong, exceptional vigor. There are no characteristics of aneuploidy or aberrant growth habit.

DESCRIPTION OF THE FLOWER

The outstanding merit and most distinguishing feature of the new variety is the delicate coloring of the flower, its exceptional substance, and massive size.

In the following description, the principal colors will be specified by reference to the code numbers of the British Horticultural Colour Charts (hereinafter BHCC number). A peripheral area of each petal, comprising most of the petal area, is a pastel rose-lilac specified in BHCC numbers as Amaranth Rose BHCC Page 139, 530 #2 to 530 #3. The peripheral rose-lilac area encloses a white central area. At the center of the white central area is a softly bordered patch of yellow resembling Yellow BHCC Page 143, 602 #1 to 602 #2. Sepals are the same rose lilac color as the petals. The texture of both petals and sepals is sparkling, clear, and of delicate coloration. The flowers hold their color well in comparison with the flowers of the Blc. Pamela Hetherington parent plant, and similar hybrids.

The full and shapely labellum of the flowers is semi-enclosed over the column. The margins of the labellum are a rose-lilac very similar to the coloring of the petals and sepals. The central portion of the labellum shades into the previously mentioned yellow (BHCC 602 #1 to 602 #2).

The flowers of the new variety Blc. Pamela Hetherington Coronation are larger and stronger in structure than other Pamela Hetherington orchids. The flowers average 12.5 to 20 centimeters in width for the entire flower.

The new variety often carries three to five of these large flowers on the stem of a mature, well grown plant. The flowers are perfectly carried on strong erect flower spikes, each flower separated from others on the stem. Petals are flat and well carried, without twisting, turning, or recurving. The tepals are in symmetrical balance with the lip and create an attractive round shape to the flower as a whole. The flowers retain color and shape for three to four weeks, a longer period of time than most orchids of similar breeding. They do not fade, spot or twist during that extended period. The flowers have a delicate fragrance throughout their life on the plant.

The blooming season is primarily throughout the month of December. However, the new variety will often bloom on growths preceding or following December, in addition to blooming during the main December blooming season.

The above combination of superior characteristics of the flowers of the new variety make them of superior value in the commercial cut flower market.

I claim:

1. A new and distinct variety of hybrid orchid, substantially as described and illustrated herein, and distinguished from its parent (grex Blc. Pamela Hetherington) and other orchids by its combination of delicate, lilac-rose flower color, superior flower substance, strength of stem structure, and vigorous, reliable blooming.

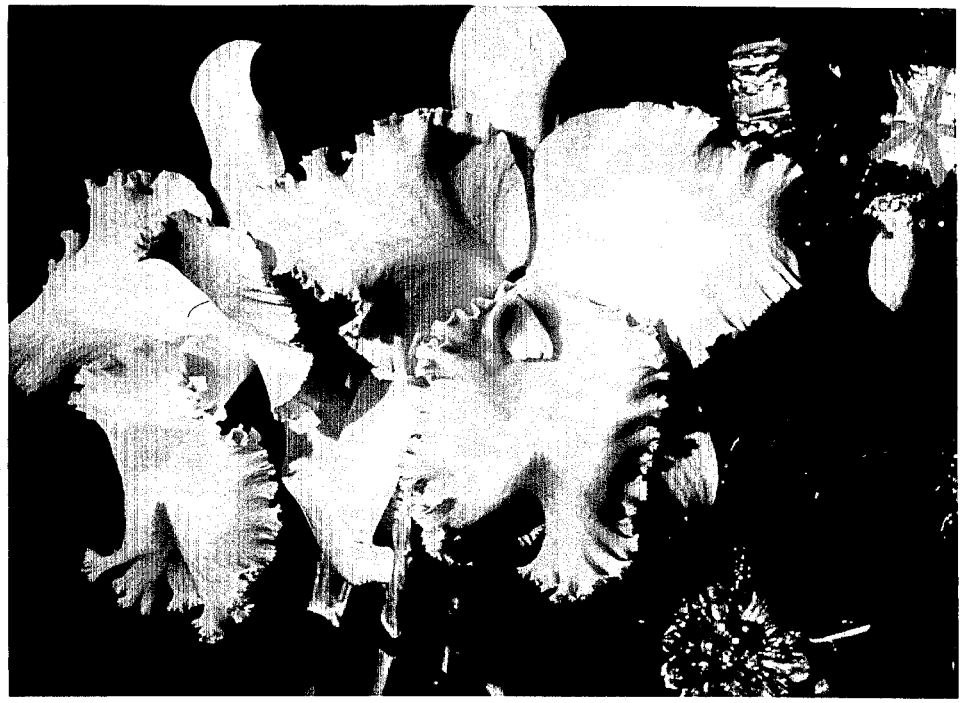
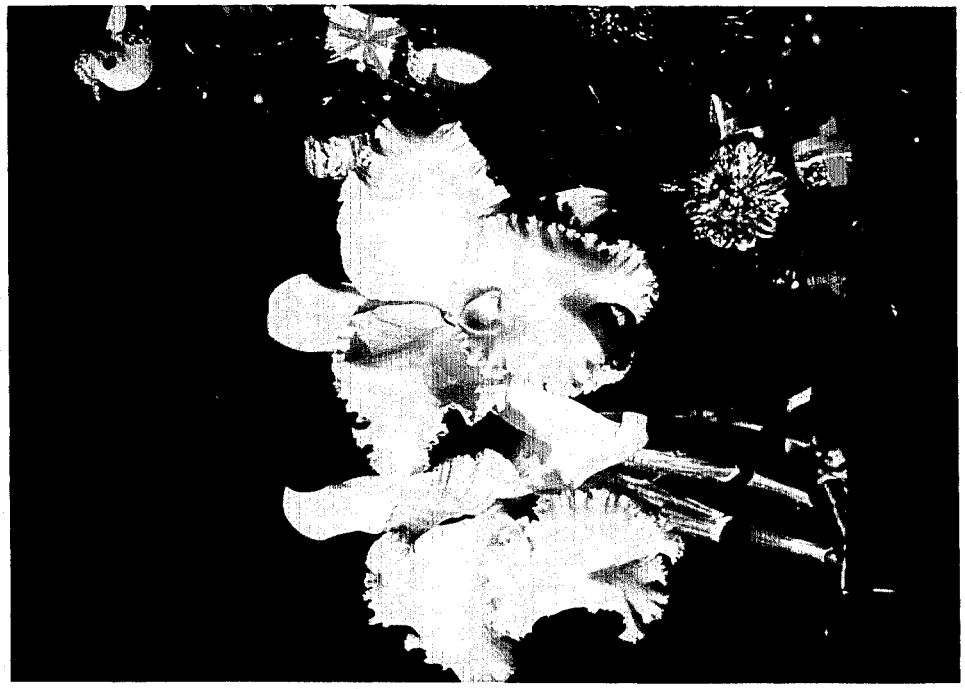

* * * * *